United States Patent [19]

Palmer

[11] 4,337,044
[45] Jun. 29, 1982

[54] NIGHT VISION TRAINING SIMULATOR

[75] Inventor: John E. Palmer, Springfield, Va.

[73] Assignee: The United States of America as represented by the Secretary of the Army, Washington, D.C.

[21] Appl. No.: 232,333

[22] Filed: Feb. 6, 1981

[51] Int. Cl.³ .............................................. G09B 19/00
[52] U.S. Cl. ....................................... 434/11; 350/1.1; 40/364; 40/367
[58] Field of Search ........................ 434/11, 16, 17, 19, 434/20, 21, 22, 26, 27; 350/1.1, 1.2, 1.3, 1.4, 1.5, 1.6; 40/361, 362, 363, 364, 365, 366, 367

[56] References Cited

U.S. PATENT DOCUMENTS

| 2,418,605 | 4/1947 | Shepherd, Jr. et al. | 350/1.1 |
| 2,521,571 | 9/1950 | Du Mont et al. | 350/1.1 X |
| 2,550,799 | 5/1951 | Fuller | 40/364 |
| 2,856,540 | 10/1958 | Warshaw | 350/1.4 X |
| 3,554,628 | 1/1971 | Kennedy | 350/1.2 |
| 3,588,237 | 6/1971 | Aldrich | 434/20 X |
| 3,691,284 | 9/1972 | Borjeson | 434/20 |
| 3,839,192 | 8/1974 | Wheeler | 350/1.1 |
| 3,958,871 | 5/1976 | Rosendahl et al. | 434/20 X |
| 4,027,160 | 5/1977 | Driffield et al. | 350/1.3 X |
| 4,240,212 | 12/1980 | Marshall et al. | 434/11 |

Primary Examiner—William H. Grieb
Attorney, Agent, or Firm—Nathan Edelberg; Milton W. Lee; John E. Holford

[57] ABSTRACT

The present invention provides a training aid and method that produces realistic colored images of targets, as seen through a thermal viewer, using black and white video or photographic techniques with filters and light modulators.

10 Claims, 4 Drawing Figures

NIGHT VISION TRAINING SIMULATOR

The invention described herein may be manufactured, used and licensed by the U.S. Government for governmental purposes without the payment of any royalties.

BACKGROUND OF THE INVENTION

1. Field of the Invention.

The invention is related to a class of devices known as thermal viewers. There are many devices that fall in this category including a variety of image orthicons having retinas responsive to very long wavelengths of infrared light, e.g. greater than one micron. Most of the current devices, however, utilize small individual detecting elements or diodes over which the infrared image is scanned. A very popular device at present uses a row of diodes equal in length to one dimension of the infrared image. The output of these detectors produces a video type signal that can be processed in various ways to provide a visible image. One way is to convert the information to a normal TV format and display the image on a commerical TV receiver. Another way is to provide a receiver with scan signals to match the mirror scanned image in the thermal viewer. One simple technique widely used is to provide a light emitting diode coupled to each detector and to scan the visible image thus produced using the silvered back of the same mirror that scans the infrared image. The image obtained though usually recognizable is quite different from a normal image of the target or scene being observed. This is due mainly to the fact that the image is emitted by rather than reflected from the target and is proportional to the temperature of its various areas. It is also partly due to the constrainst of the viewer itself involving mainly the size of the detectors, their total response and the rate at which they respond. The information available in these images, although much less than that generally found in reflected light images, is none-the-less valuable because the information is nearly one hundred percent dependent on the character of the target and is very difficult to camouflage. To utilize this information, however, there must be a course of training to provide the observer with comprehensive background experience in its interpretation.

2. Description of the Prior Art.

The images produced by thermal viewers have been recorded in the past with black and white as well as color photography. Since the viewers are still relatively expensive and scarce, the use of photographic images for trainee users is very compelling. The latter also aleviates the problem of providing real targets such as tanks, planes and even large ground installations. Thus far, however, the photographic approach has been unsatisfying. Even color photography lacks the realistic, live environment essential to proper training.

SUMMARY OF THE INVENTION

The invention overcomes these prior art difficulties with a combination of black and white photographic or video techniques with a variety of optical devices includidng a special filter.

BRIEF DESCRIPTION OF THE DRAWINGS

The invention is best understood with reference to the accompanying drawings wherein.

DESCRIPTION OF THE PREFERRED EMBODIMENT

Figure 1:
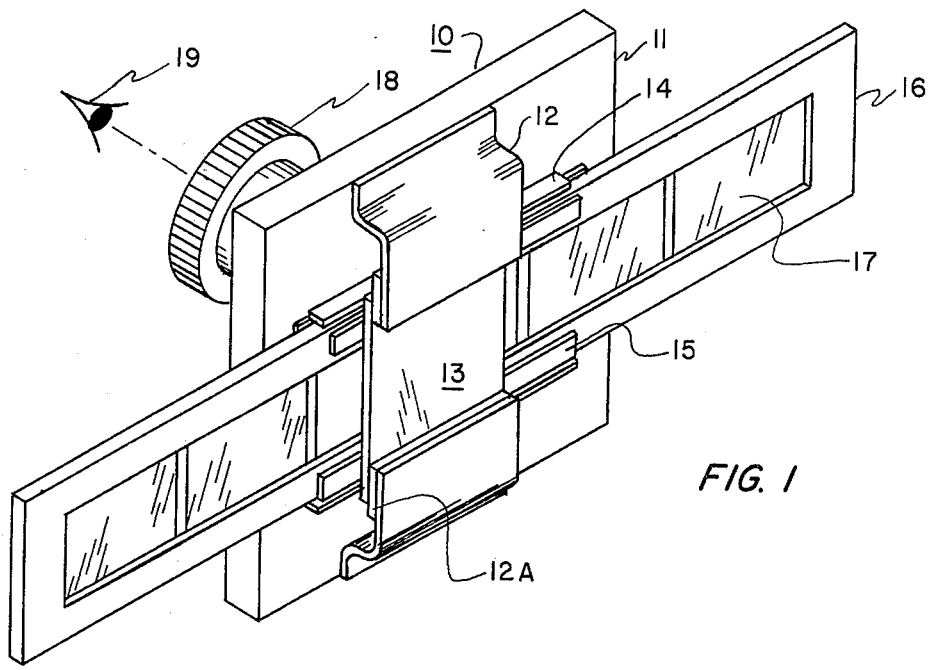
FIG. 1 shows a basic training viewer according to the present invention.

Referring specifically to FIG. 1, there is shown a handheld viewer 10 designed specifically for the purposes of the invention. The viewer includes a housing member 11 with a central aperture and a pair of brackets 12 which each carry a resilient mounting strip 12A. The mounting strips are cemented to the edge of a filter 13. A guide channel 14 formed from sheet metal is attached to the block and covers the central aperture, the channel having a matching aperture in its center aligned with the housing aperture. Additional resilient strips 15 are mounted on the opposite side of the filter along the same edge portions of the filter as strips 12A. A standard film strip carrier 16 slides snugly but freely in the channel member under a slight pressure from strips 15. An eyepiece 18 designed to match the 35 mm image format without vignetting and providing a magnification and a focal length identical to the thermal viewer is mounted in the central aperture and focussed on the film strip. The eye 19 of the trainee thus experiences approximately the same angle of view, eye relief, and image size as the operator of a thermal viewer.

The film strip 17 carries a plurality of pictures or images of targets having contrast of the same order as provided by the light emitting elements of a thermal viewer. The strip is in fact a record of such images obtained by photographing the light emitting elements while the operating thermal viewer is focussed on the targets in question. Black and white film captures this contrast more faithfully than does color film with its multilayer filter structures. To restore the original color the film 13 is carefully chosen. It has been found that a filter 2" square 1PL Limited Red NBS 3215-60-7 provides an outstanding match when the images are viewed by the light from a tungsten or daylight source. This arrangement permits the trainee to learn the infrared signatures of many targets with very little effort or expense.

Figure 2:
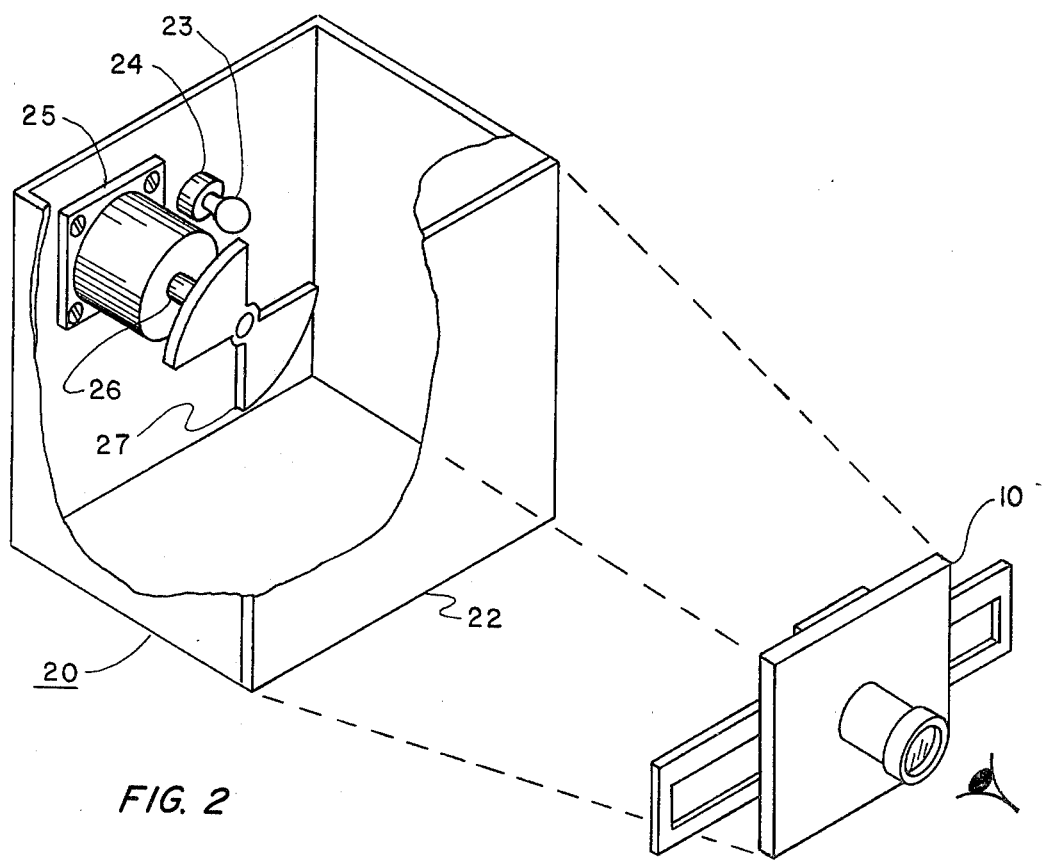
FIG. 2 shows the combination of the viewer of FIG. 1 with a simple modulated light source.

FIG. 2 shows the same handheld viewer 10 in combination with a special lightbox 20. The lightbox is merely a housing 21 with a translucent light diffuser plate 22 forming the front wall. A tungsten light bulb 23 and socket 24 are mounted on the backwall and wired to any convenient power source (not shown) in or outside of the lightbox. A motor 25 is mounted on the same wall with a shaft 26 that extends further from the backwall than the light bulb. A chopper wheel 27 is mounted at the extreme end of the shaft and rotates in front of the light bulb. If the power source for the motor is a standard alternator, the motor can be of the synchronous type and the chopper blade can be designed to produce the same light modulations present in the thermal viewer due to the scan mirror. A variable speed motor with a control adjustment for speed will do the same. This permits the trainee to adapt himself to long periods of continuous observation and to ignore this effect when evaluating real targets.

Figure 3:
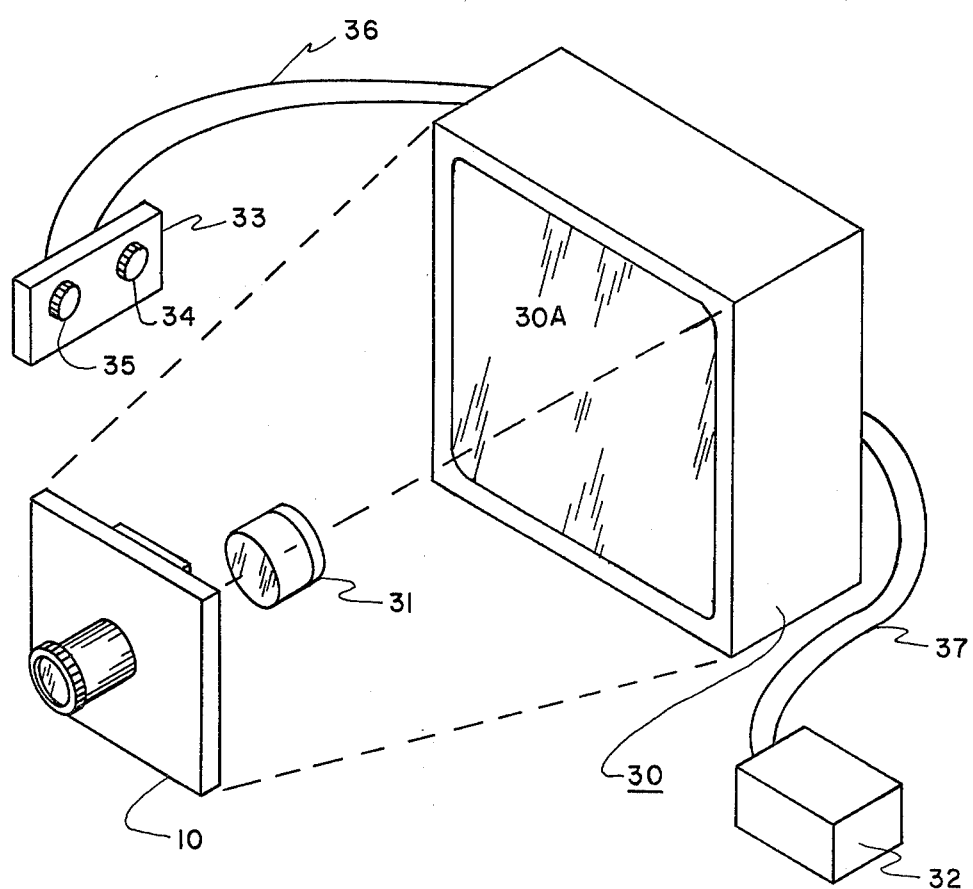
FIG. 3 shows the combination of the FIG. 1 viewer with a TV type receiver.

FIG. 3 shows a far more versatile arrangement that allows for viewing of moving targets. The viewer is shown in combination with a TV type receiver 30 and a medium focal length intermediate lens 31. The target information in this arrangement is best recorded on video tape. A video tape player 32 can then be wired by a cable 37 to the video input of the receiver to display the recorded night sight image. The information can be directly recorded from the real thermal sight using a video camera or transferred from a photographic image using video recording techniques well known in the art. The medium focal length intermediate lens forms a 35 mm image on the TV screen at the focal plane of the eyepiece of the handheld training viewer 10. The image size can be adjusted to provide the same angle of view as a thermal viewer. A pair of contrast and brightness controls 34 and 35 are mounted in a control box 33 wired by leads 36 to the appropriate portions of the TV receiver circuits. The control box is located adjacent to and preferably on the training viewer 10. The trainee can thus exercise the similar control over the brightness and contrast image controls that the operator of a thermal viewer can. For further realism a mock up of the actual thermal viewer housing can be made to contain the video monitor, the intermediate lens and the training viewer. The monitor brightness and contrast controls can be wired into the actual brightness and gain control pots of the mock up viewer so the trainee will actually manipulate the same controls for image quality as he would on the actual thermal viewer. Since the images can vary with time, the sintillation effect of the light box of FIG. 2 will already be present. The new dimension of moving images is also present. Image information can be broadcast to any number of such receivers from a central records means or can even be generated live or delayed from remote locations, even military vehicles, aircraft or ships carrying thermal viewers.

Figure 4:
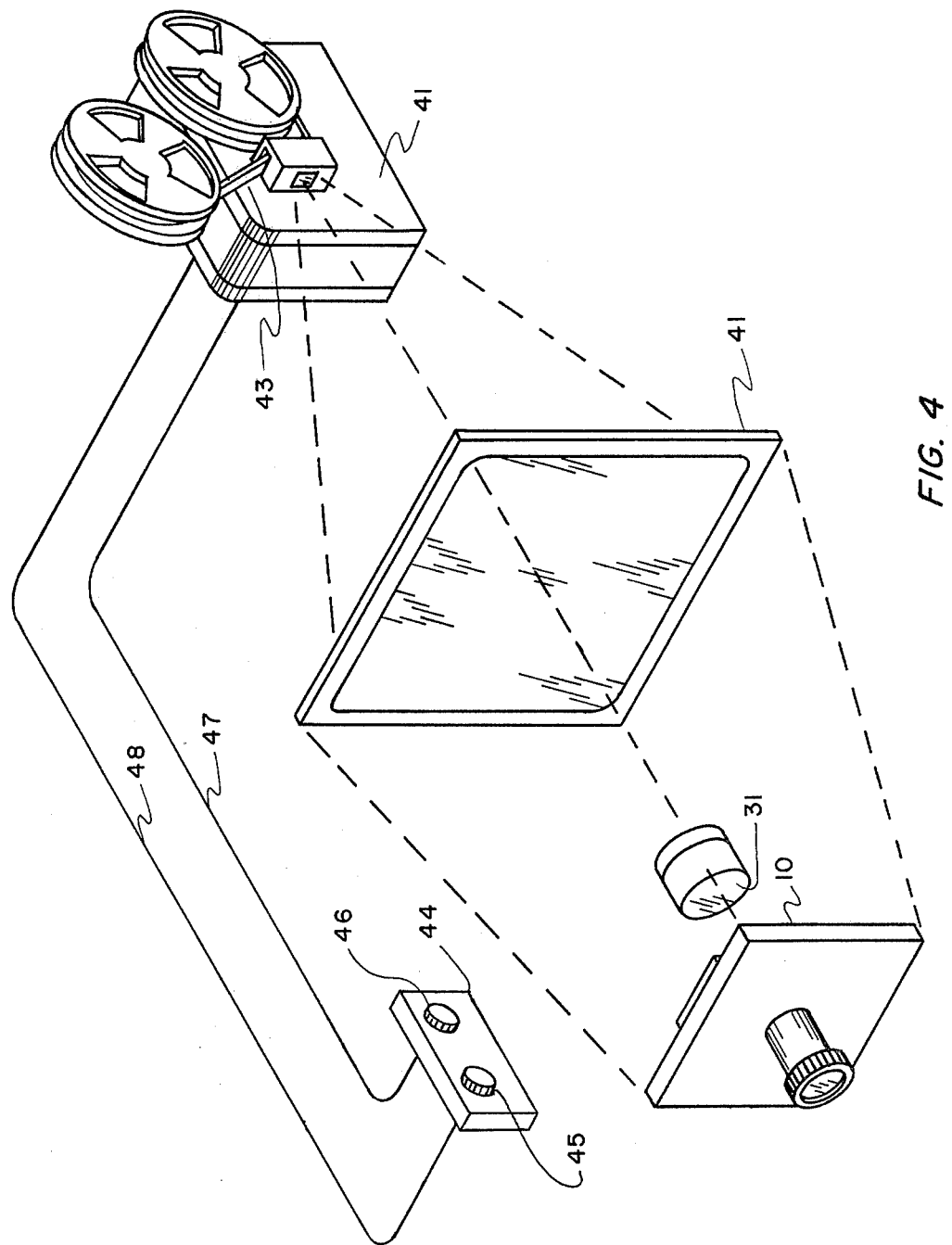
FIG. 4 shows the combination of the viewer of FIG. 1 with a motion picture projector.

FIG. 4 shows another arrangement which has separate advantages. Instead of a TV screen, a backlighted movie projection screen 41 is provided. The IR image is projected on this screen by a moving picture projector 42. Since the images are produced from a continuous film strip 43, a great deal of faithfully reproduced information can be easily stored at minimum expense. This arrangement can also have a control box 44. One control 45 can vary brightness by directly or indirectly varying the current to the projector through lead 47 and the other 46 can control the projector speed for special effects and study by the trainee.

Many variations of the above devices and methods will immediately occur to those skilled in the art but the invention is not limited except by the claims which follow.

I claim:

1. A training aid to simulate the light images of a plurality of diverse targets created by the light emitting elements in a thermal viewer comprising:
    a source of white light;
    a record means optically coupled to said source to transform light from said source into a black and white image of said targets closely resembling the same target image produced by said viewer;
    an eyepiece means coupled to said record means to focus said image for comfortable viewing; and
    a light filter means mounted between said source and said eyepiece means to pass substantially only those quanta of light having the same frequency and spectral distribution as said light emitting elements.

2. A training aid accordidng to claim 1 wherein:
    said record means is a strip of black and white film beaming images of said targets produced by exposing said film through a camera to said image created by the light emitting elements.

3. A training aid according to claim 1 wherein said record means includes:
    a light reflective screen;
    a reel of motion film exposed through a motion picture camera to the images of moving targets created by said light emitting elements; and
    a motion picture projector directing light from said source through said film and focussing the images thereon onto said screen.

4. A training aid according to claim 1 wherein said source and record means include:
    a television receiver; and
    a video recorder connected to a video input of said television receiver.

5. A training aid in accordance with claims 1, 2, 3, or 4 wherein:
    said source includes a remote element to vary the brightness of said source, said remote element being located adjacent said eyepiece.

6. A training aid in accordance with claim 4 wherein said television includes:
    a remote element to vary the contrast thereof, said remote element being located adjacent said eyepiece.

7. A training aid in accordance with claim 1, 2, 3, or 4 further including:
    a light chopper means mounted between said source and said eyepiece to modulate the light from said source at the field repetition rate of said thermal viewer.

8. The methods of simulating the images of a series of diverse targets created by the light emitting elements of a thermal viewer comprising the steps of:
    recording only the amplitude of the light emitted by each element;
    recreating the pattern of said amplitudes in beams of white light; and
    filtering out the spectral components of said white light not present in the spectrum of said light emitting elements.

9. The method according to claim 8 further including the step of:
    modulating said beams of white light at the field repetition rate of said thermal viewer.

10. The method according to claims 8 or 9 further including the step of:
    varying the relative amplitudes of said beams by an amount directly proportional to their initial amplitude, thereby producing contrast changes in the simulated image.

* * * * *